United States Patent [19]

Garber et al.

[11] 3,952,010

[45] Apr. 20, 1976

[54] CATALYTIC DEHYDROGENATION PROCESS FOR THE PREPARATION OF 3,5-DISUBSTITUTED PYRAZOLES

[75] Inventors: Murray Garber, Trenton; Lawrence James Ross, Martinsville; Walter Joseph Stepek, Trenton, all of N.J.

[73] Assignee: American Cyanamid Company, Stamford, Conn.

[22] Filed: Feb. 12, 1975

[21] Appl. No.: 549,219

Related U.S. Application Data

[63] Continuation-in-part of Ser. No. 398,284, Sept. 17, 1973, abandoned.

[52] U.S. Cl. .................. 260/310 R; 260/310 D; 260/311
[51] Int. Cl.² .................. C07D 49/02; C07D 57/00; C07D 99/00
[58] Field of Search .................. 260/310 R, 310 D

[56] References Cited
FOREIGN PATENTS OR APPLICATIONS
641,015   8/1950   United Kingdom ............ 260/310 R OTHER PUBLICATIONS
Chemical Abstracts, Vol. 52: 11013$f$ (1958).
Chemical Abstracts, Vol. 79: 136707$z$ (1973).

*Primary Examiner*—Donald B. Moyer
*Attorney, Agent, or Firm*—Harry H. Kline

[57] ABSTRACT

There is provided a process for the preparation of 3,5-disubstituted pyrazoles which involves:

a. the reaction of a methyl ketone, such as acetophenone or an appropriate derivative thereof, with an appropriate aldehyde, such as benzaldehyde in the presence of base to form a 1,3-disubstituted $\alpha,\beta$-unsaturated ketone, such as chalcone or a substituted chalcone, b. the acidification of said $\alpha,\beta$-unsaturated ketone, followed by treatment of the acidified reaction mixture with hydrazine to form a disubstituted pyrazoline, and c. the catalytic dehydrogenation of said pyrazoline to yield the desired 3,5-disubstituted pyrazole.

11 Claims, No Drawings

CATALYTIC DEHYDROGENATION PROCESS FOR THE PREPARATION OF 3,5-DISUBSTITUTED PYRAZOLES

This application is a continuation-in-part of our co-pending application, Ser. No. 398,284, filed on Sept. 17, 1973, now abandoned.

The present invention relates to a process for the manufacture of 3,5-disubstituted pyrazoles. More particularly, it relates to (a) the reaction of a methyl ketone, such as acetophenone or an appropriate derivative thereof, with an appropriate aldehyde, such as benzaldehyde, in the presence of base to form a 1,3-disubstituted $\alpha, \beta$- unsaturated ketone, such as chalcone or a substituted chalcone, (b) the acidification of said $\alpha, \beta$-unsaturated ketone, followed by treatment of the acidified reaction mixture with hydrazine to form a disubstituted pyrazoline, and (c) the catalytic dehydrogenation of said pyrazoline to obtain the desired 3,5-disubstituted pyrazole in good yield and purity.

In general, the overall reaction can be illustrated graphically as follows:

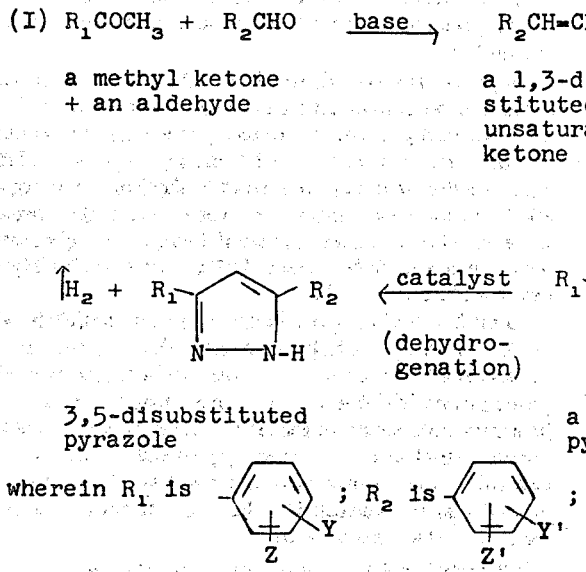

wherein $R_1$ is a phenyl group substituted with Z and Y; $R_2$ is a phenyl group substituted with Z' and Y'; and Y, Y', Z and Z' each independently represent members selected from the group consisting of hydrogen, halogen, methylthio, methylsulfonyl, cyano, carboxyl, carboalkoxy $C_1$–$C_4$, hydroxy, alkyl $C_1$–$C_4$, haloalkyl $C_1$–$C_4$ containing 1 to 4 halogen atoms, and alkoxy $C_1$–$C_4$.

The term "halogen", as herein used, is intended to mean fluorine, chlorine, iodine or bromine; however, fluorine, chlorine and bromine are preferred.

The terms "alkyl" and "alkoxy" are intended to mean straight chain and branched chain alkyl and alkoxy, including straight and branched haloalkyl, and straight and branched carboalkoxy.

In accordance with the process of this invention, approximately equimolar amounts of the ketone, $R_1COCH_3$, and the aldehyde, $R_2CHO$, are charged to a reactor along with a quantity of a $C_1$–$C_4$ alcohol, preferably methanol. Approximately one-half mole of base per mole of ketone is then slowly added to the reaction mixture while maintaining the temperature thereof between about 10°C. and 70°C., and preferably between 20°C. and 30°C.

Exemplary bases include, for instance, alkali metal $C_1$–$C_4$ alkoxides, such as sodium or potassium methoxide, ethoxide, propoxide, butoxide, t-butoxide, and equivalents thereof, or aqueous sodium hydroxide or potassium hydroxide. Aqueous sodium hydroxide is, however, generally preferred.

The aforementioned ketone-aldehyde mixture is stirred, usually for several hours, and then acidified to a pH of 7 or below, preferably to between 5 and 7, utilizing a mineral acid such as hydrochloric acid, sulfuric acid or phosphoric acid. In practice, it will usually be found that the mole ratio of acid required for pH adjustment will approximate the mole ratio of base employed in the previous reaction.

Subsequent to acidification, the reaction mixture is treated with at least one mole equivalent, or more, of hydrazine. The hydrazine employed may be anhydrous or in aqueous solution, and should be introduced into the reaction mixture in such manner as to maintain the temperature thereof below 70°C. and, preferably, between 20°C. and 50°C. Since the reaction is exothermic, cooling is generally required to maintain the latter temperatures. Further, the reaction is preferably carried out in an inert atmosphere in order to exclude air from the reaction mixture and, thus, prevent any oxidation of the intermediate pyrazoline. This can be achieved by conducting said reaction under a blanket of an inert gas, such as nitrogen, helium, argon or carbon dioxide. In general, the hydrazine addition period should be relatively rapid, since prolonged additions result in lower product yield. It is a good practice to complete the hydrazine addition within about sixty minutes, or less, both in a batch or continuous operation.

Following the hydrazine addition, the reaction mixture is heated to reflux, and subjected to catalytic dehydrogenation. This catalytic dehydrogenation reaction is preferably carried out in an inert atmosphere, as for example, under a blanket of nitrogen, argon, helium or carbon dioxide. However, the provision for an inert atmosphere is not absolutely essential, although it does improve product yield. The dehydrogenation can be carried out in a variety of [selected] solvents or solvent mixtures by first distilling off the alcohol and replacing it with the selected solvent. The preferred solvent is xylene per se or any available mixtures of ortho, meta and para xylenes. However, other solvents are suitable. Examplary solvents include, for instance, (a) benzene, toluene, heavy aromatic solvents, such as PANASOL AN-2, AN-3 or AN-5, ESSO HAN, SOCAL 44 L, and the like, which have a mixed aniline point above 30°F. but not exceeding 95°F., an aromatic content between 60% and 100% and a specific gravity at 60°160%F. between 0.88 and 1.5; (b) cyclic ethers such as dioxane and tetrahydrofuran (THF); (c) polar aprotic solvents such as acetonitrile and dimethylformamide (DMF); or (d) chlorinated hydrocarbons, such as chloroform, perchloroethylene or ethylene dichloride. After the alcohol solvent is removed by distillation, and the selected solvent from the above-mentioned group of solvents, preferably xylenes or mixed xylenes, is added, the reaction mixture is cooled to between 40°C. and 70°C., and washed with water to remove alkali metal salts, alcohol and any unreacted hydrazine. In the preferred procedure, a dehydrogenation catalyst, such as platinum, palladium, platinium on silica, platinum on barium sulfate, platinum on carbon, palladium on carbon, or prereduced copper chromite, is added to the reaction mixture while maintaining an inert gas flow over the reaction mixtrue. In practice, the catalyst should be introduced to the charge (at a temperature between 40°C. to 60°C.) as a water wet solid or admixed in a solvent as a slurry.

The overall reaction mixture is then brought to reflux and residual water removed by azeotropic distillation. Refluxing is continued while maintaining an inert gas flow to insure both complete removal of hydrogen gas from the reaction system and to obtain completion of the reaction. When, for instance, prereduced copper chromite is used as the specific dehydrogenation catalyst, a reaction temperature of about 200°C. is required and, therefore, a heavy aromatic solvent with a minimum boiling point of about 200°C. is used.

After completion of the dehydrogenation stage, the catalyst can be removed by filtration at a temperature of about 130°C., or at a lower temperature, 95°C. to 110°C., by the addition of a co-solvent such as dimethylformamide in which the product 3,5-disubstituted pyrazole is more soluble. The filtrate is cooled, preferably to about 10°C., and the 3,5-disubstituted pyrazole, prepared by the above reaction, is then separated from the filtrate. Separation may be accomplished by any convenient means, as for example, by centrifugation or filtration.

As an alternative procedure, the dehydrogenation mixture from the above reaction containing the 3,5-disubstituted pyrazole and the catalyst, can be employed directly without separation in the preparation of 1-alkyl-3,5-disubstituted pyrazole. This eliminates the need for a hot catalyst filtration, because the 1-alkyl-3,5-disubstituted pyrazole is extremely soluble in the reaction solvent, and the catalyst can then be removed after the alkylation step merely by room temperature filtration. The catalyst can then be recycled to prepare another batch of 3,5-disubstituted pyrazole.

As hereinabove mentioned, catalytic dehydrogenation can also be carried out in a $C_1$–$C_4$ alcohol, preferably methanol or ethanol, employing palladium on carbon or platinum on carbon as the catalyst. This procedure does not require distillation of a portion of the alcohol and substitution thereof with a solvent, such as xylene or mixed xylenes. However, dehydrogenation in alcohol proceeds more slowly than it does in the preferred co-solvent system, and product yields are generally lower than those obtained with said system. These results are primarily due to the lower boiling point of the alcohol, and to the greater solubility of 3,5-disubstituted pyrazole in alcohol. After a hot filtration to remove the catalyst from the reaction mixture, resultant mixture is cooled to about 10°C. The pyrazole precipitates and can be separated by filtration or centrifugation. If desired, water can be added to the reaction mixture after separation of the catalyst, to improve pyrazole precipitation and separation from the reaction mixture.

The 3,5-disubstituted pyrazoles prepared in accordance with the process of this invention have a variety of uses, among which is the utilization thereof as intermediates for the preparation of 1,2-dialkyl-3,5-disubstituted pyrazolium salts, such as 1,2-dimethyl-3,5-diphenylpyrazolium methyl sulfate. These pyrazolium salts are highly effective herbicidal agents and are particularly effective for the selective control of wild oats in the presence of small grains such as barley, wheat, rye and rape.

As previously stated, resultant 3,5-disubstituted pyrazole can be converted to a corresponding 1-alkyl-3,5-disubstituted pyrazole by reacting it with an equimolar amount or excess (i.e. 1 to 1.5 moles) of an alkylating agent in the presence of a solid, anhydrous, inorganic alkali metal base and a non-aqueous, inert, organic solvent. The reaction is carried out at a temperature between about 50°C. and 175°C., and preferably between 85°C. and 120°C.

Suitable alkylating reagents include alkyl halides, dialkyl sulfates, alkyl phosphates, alkyl hydrogen sulfates, or alkyl toluene sulfonates; wherein said alkyl groups contain from 1 to 4 carbon atoms. Among the preferred alkylating reagents are alkyl halides, such as methyl, ethyl, n-propyl, isopropyl, n-butyl and isobutyl chlorides and bromides; dialkyl sulfates, such as dimethyl sulfate and alkyl toluene sulfonates, such as methyl p-toluene sulfonate.

Illustrative solvents which may be employed herein are non-aqueous, inert, organic solvents, preferably selected from aromatic hydrocarbons, such as toluene and xylene; aliphatic hydrocarbons such as hexane and heptane; ketones having from 4 to 7 carbon atoms, such as methyl isobutyl ketone, cyclohexanone, or the like; alcohols having from 2 to 8 carbon atoms, and preferably 3 to 4 carbon atoms; dipolar aprotic solvents, such as dimethyl sulfoxide, dimethyl formamide, acetonitrile, nitrobenzene, N,N-dimethylacetamide, tetrahydrosulfolane; ethylene dichloride; and alkoxyalkyl ethers, such as dioxane and tetrahydrofuran.

Suitable bases are solid, anhydrous, inorganic, alkali metal bases. They are strong bases, and preferably selected from the group consisting of sodium hydroxide, potassium hydroxide, sodium carbonate, potassium carbonate, calcium oxide and calcium hydroxide.

Conversion of the 3,5-disubstituted pyrazoles to the 1-alkyl-3,5-disubstituted pyrazoles can be graphically illustrated as follows:

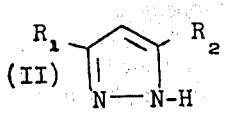 + $(R_3)_m Q$ + Base $\longrightarrow$ 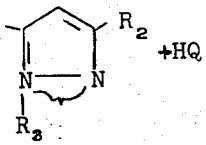 +HQ (II)

wherein $R_1$ and $R_2$ are as defined above in (I); $R_3$ is an alkyl radical of from 1 to 4 carbon atoms, Q is a radical selected from the group consisting of a halide, a sulfate, a phosphate, toluene sulfonate and a hydrogen sulfate; and m represents an integer selected from 1 to 3.

Resultant 1-alkyl-3,5-disubstituted pyrazole is then readily converted to the herbicidally active 1,2-dialkyl-3,5-disubstituted pyrazolium salt by quaternization of the 1-alkyl-3,5-disubstituted pyrazole.

Conversion of the 1-alkyl-3,5-disubstituted pyrazole to the 1,2-dialkyl-3,5-disubstituted pyrazolium salt is achieved by reacting the pyrazole with an equimolar amount or a slight excess of an alkylating reagent $(R_4)_m Q$, where $R_4$ is alkyl $C_1$-$C_4$ and m and Q are as defined above. Alkylating reagents that can be used are selected from the the group consisting of alkyl halides, dialkyl sulfates, and alkyl toluene sulfonates. They are used in equimolar amounts with the pyrazole or in a slight excess, for example, from about 1 to 1.5 moles per mole of pyrazole.

In general, the latter reaction is carried out in the presence of a non-aqueous organic solvent, such as xylene or in a mixture of inert organic solvents consisting of (a) a chlorinated hydrocarbon solvent, and (b) an organic solvent selected from the group consisting of aromatic hydrocarbons, aliphatic hydrocarbons, ketones, alcohols, alkoxyalkyl ethers, dipolar aprotic solvents and cyclic ethers as defined above. Preferred mixtures generally consist of from about 10% to 90%, preferably 25% to 75%, by volume of a solvent in which the quaternized 3,5-disubstituted pyrazolium salt is relatively insoluble, and from about 90% to 10%, preferably 75% to 25%, of a solvent in which the quaternized 3,5-disubstituted pyrazolium salt is relatively soluble. Preferred co-solvent systems meet the above requirements as to percent composition, and are selected from aromatic hydrocarbon solvents in admixture with chlorinated hydrocarbon solvents or aliphatic hydrocarbon solvents in admixture with chlorinated hydrocarbon solvents. particularly advantageous are xylene-ethylene dichloride mixtures. The latter compositions are especially useful, since they provide a readily filterable, flowable slurry from which the quaternized 3,5-disubstituted pyrazolium salt is readily recovered. The use of the co-solvent system assures excellent yields of very high purity product and avoids the production of mixtures of quaternized 3,5-disubstituted pyrazolium salts. This alkylation is carried out in a manner which assures that the temperature of the reaction mixture is generally maintained between about 50°C. and 175°C., and preferably between 90°C. and 110°C.

The reaction mixture containing the pyrazolium salt is cooled and the pyrazolium salt then separated from the reaction mixture. Alternatively, the reaction mixture may be heated with a tertiary-amine to destroy residual alkylating agent, cooled and then centrifuged or filtered to recover the pyrazolium salt. Yet another alternative is to extract the pyrazolium salt with water from the above-mentioned reaction mixture. The water solution thus obtained may then be employed directly in the control of undesirable plant species.

The above reaction and the herbicidally effective 1,2-dialkyl-3,5-disubstituted pyrazolium salts, which can be prepared by said reaction, is illustrated as follows:

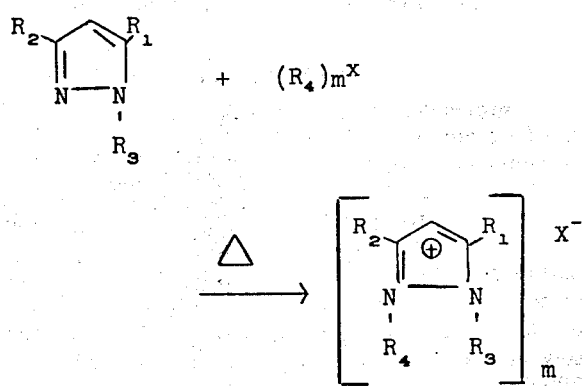

where $R_1$, $R_2$, $R_3$ and $R_4$ are as described above; X represents an anion having a charge from 1 to 3; and m is an integer selected from 1, 2 and 3.

Illustrative of the anions which are suitable for use in the present invention may be mentioned, for example, halides such as chloride, bromide or iodide; sulfate; hydrogen sulfate; methyl sulfate; benzene sulfonate; $C_1$-$C_4$ alkoxy benzene sulfonate; $C_1$-$C_4$ alkyl benzene sulfonate, preferably a toluene sulfonate such as p-toluene sulfonate; phosphate and methyl phosphates; and alkane sulfonate $C_1$-$C_4$.

The following examples are presented primarily for purposes of illustrating more specific details of the invention which are not to be taken as limitative. Unless otherwise specified, the parts are by weight and the analyses are in percent.

EXAMPLE 1

The preparation of 3,5-diphenylpyrazole

Acetophenone (31.85 parts), benzaldehyde (28.13 parts) and methanol (157.58 parts) are charged to a suitable reactor, and 50% aqueous sodium hydroxide (10.61 parts) is then added at 20°C. to 30°C. The reaction mixture is stirred for 4 hours at 20°C. to 30°C. After the hold period, the resultant chalcone slurry is made slightly acidic (pH 5 to 7) by the addition of 36% hydrochloride acid. The reaction mixture is cooled to −5°C. to 0°C. Nitrogen is introduced over the reaction mixture, and 20.86 parts of 70% hydrazine hydrate is added at a maximum temperature of 35°C. After the hydrazine hydrate addition, the reaction mixture is stirred at 20°C. to 30°C. for 1 hour. Approximately 75% to 80% of the methanol is then distilled off and replaced with mixed xylenes. The xylene solution is cooled to 50°C. to 60° C. and washed twice with water to remove sodium chloride, methanol and unreacted hydrazine hydrate.

After the last water wash, 2.20 parts of 5% palladium on carbon carbon catalyst is added under nitrogen, and the reaction mixture heated to reflux (140°C. to 144°C.) and held at reflux for 2 hours. A small amount of water is azeotropically removed during the heat-up and the xylene returned to the reactor. Hydrogen is evolved during the heat-up and during the 2-hour hold period at reflux. After the hold period, 15.0 parts of dimethylformamide is added, and the catalyst removed by a hot (120°C.) filtration. The catalyst is washed with xylene and then steamed to remove trace impurities and recycled for reuse. Water (53.1 parts) is added to the catalyst-free filtrate and the mixture cooled to 10°C. 3,5-diphenylpyrazole is filtered. About 43.2 parts of 3,5-diphenylpyrazole (dry basis) is obtained. This amounts to a 74% yield based on the acetophenone reactant.

EXAMPLE 2

The procedure of Example 1 is repeated in every detail except platinum on carbon is substituted for palladium on carbon. Substantially the same results are obtained. In another run, prereduced copper chromite is substituted for palladium on carbon utilizing the procedure of Example 1. However, approximately 0.5 part of prereduced copper chromite per gram mole of acetophenone is utilized, and the dehydrogenation is conducted in the presence of a high boiling aromatic solvent, PANASOLL AN-2, at a temperature of about 200°C.

Following the above procedure, but substituting the appropriate ketone and aldehyde for acetophenone and benzaldehyde, respectively, the following pyrazoles are obtained as set forth in Table I below.

TABLE I

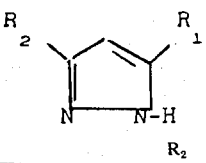

| R₁ | R₂ |
|---|---|
| 2-chlorophenyl | phenyl |
| 3-chlorophenyl | phenyl |
| 4-fluorophenyl | phenyl |
| 2-methylphenyl | phenyl |
| 4-t-butylphenyl | phenyl |
| 2-hydroxyphenyl | phenyl |
| 3-methoxyphenyl | phenyl |
| 4-methylthiophenyl | phenyl |
| 3-methylsulfonyl-phenyl | phenyl |
| 2-chlorophenyl | 3-methylphenyl |
| 2-chlorophenyl | 2-chlorophenyl |
| 3-chlorophenyl | 5-chlorophenyl |
| 2-methylphenyl | 2-methylphenyl |
| 4-methoxyphenyl | 4-methoxyphenyl |
| 2-chlorophenyl | 2-methoxyphenyl |
| 3-fluorophenyl | 3-fluorophenyl |
| 2,4-dichlorophenyl | 2,4-dichlorophenyl |
| 4-cyanophenyl | 4-cyanophenyl |
| 3-carboxyphenyl | phenyl |
| 4-chloromethyl-phenyl | 4-chloromethylphenyl |
| 3-carbomethoxy-phenyl | phenyl |
| 3,4-dimethylphenyl | 3,4-dimethylphenyl |
| 2,4-dimethoxyphenyl | 2,4-dimethoxyphenyl |
| 4-chloro-3-methylphenyl | 4-chloro-3-methylphenyl |
| 3,5-dibromophenyl | 3,5-dibromophenyl |

EXAMPLE 3

The preparation of o-(1-methyl-5-phenyl-3-pyrazolyl)phenol

A slurry of 5% palladium on carbon (0.6 part in 20 parts by volume of xylene) is added slowly to a cooled (5°C.) solution of o-(1-methyl-5-phenyl-2-pyrazolin-3-yl) phenol (10.5 parts) in 50 parts by volume of xylene, and the resulting suspension heated at reflux. Periodically, samples are removed for gas, liquid chromatography (glc) analysis.

When glc indicates that all of the starting material has been utilized, the reaction mixture is cooled and filtered, and then is evaporated in vacuo to give an orange-brown oil which slowly crystallizes. After drying throroughly, a product weighing 8.1 parts is obtained with melting point 90.5°C. to 93°C. This amounts to a yield of 78.2%, based on the weight of o-(1-methyl-5-phenyl-2-pyrazolium-3-yl) phenol.

Analysis calculated for $C_{16}H_{14}N_2O$: C, 76.78; H, 5.64; N, 11.19. Found: C, 76.60; H, 5.72; N, 10.63.

EXAMPLE 4

The preparation of 1-methyl-3,5-diphenylpyrazole

The procedure of Example 1 is followed in every detail except that no dimethylformamide is added during the dehydrogenation step and the catalyst is not removed. The reaction mixture is cooled to about 50°C., 2.42 parts of methyl alcohol and 11.3 parts of solid anhydrous sodium hydroxide are added. The reaction mixture is heated to 95°C. to 100°C., and 29.8 parts of dimethyl sulfate are next added. The reaction mixture is heated at reflux for about 60 minutes, then cooled to 80°C., and 82 parts of water are added. Fifty percent aqueous sodium hydroxide are added to bring the pH of the aqueous phase to between 10 and 11. The reaction mixture is filtered to recover the spent catalyst. There is no need to filter hot, because the 1-methyl-3,5-diphenylpyrazole is extremely soluble in xylene. The catalyst is washed with xylene, and water, and then recycled to a subsequent dehydrogenation batch. The aqueous layer is removed, the organic layer is washed with 82 parts or water, and the aqueous layer is removed. The organic layer contains about 41 parts of 1-methyl-3,5-diphenylpyrazole which amounts to 89.5% yield based on 3,5-diphenylpyrazole.

EXAMPLE 5

The preparation of 1-methyl-3,5-diphenylpyrazole

Five parts of 3,5-diphenylpyrazole are dissolved in 25 parts (by volume) of methyl isobutyl ketone. Solid anhydrous sodium hydroxide (1.1 parts) is added and the mixture is heated to 90°C. Dimethyl sulfate (3.43 parts) is added and the mixture is next heated to 112°C. to 115°C. The reaction mixture is sampled after 1.5 hours, and no unreacted 3,5-diphenylpyrazole is found to be present. The reaction mixture is cooled to 50°C., and 30 parts of water are added. The pH is next adjusted to between 11 and 12 by the addition of aqueous sodium hydroxide. The organic layer is washed twice with 30 parts water. For yield determination the methyl isobutyl ketone is removed in vacuo, producing 4.95 parts (93% crude yield) of an oil which crystallizes on cooling (melting point 52°C. to 53°C). Analysis of the product shows it to be 85.5% pure as 1-methyl-3,5-diphenylpyrazole.

EXAMPLE 6

The preparation of 1-methyl-3,5-diphenylpyrazole

Twenty parts of 3,5-diphenylpyrazole is dissolved in 100 parts xylene containing 7.26 parts of solid anhydrous sodium hydroxide. The reaction mixture is heated to 120°C., and 13.8 parts of dimethyl sulfate are added. The reflux temperature drops to 95°C., and after 15 minutes at 95°C., a reaction mixture sample indicates no unreacted 3,5-diphenylpyrazole is remaining (tlc.) After 30 minutes, the reaction mixture is cooled to 80°C. and 50 parts of water are added. Fifty percent aqueous sodium hydroxide is added to bring pH of aqueous phase to between 10 and 11. The organic layer is washed twice with 50 parts of water. For yield determination the xylene is removed in vacuo, producing 19.7 parts of an oil which crystallizes on seeding. Analysis of the product shows it to be 98.5% pure.

EXAMPLE 7

The preparation of 1,2-dimethyl-3,5-diphenylpyrazolium methyl sulfate

A solution of 1 mole of 1-methyl-3,5-diphenylpyrazole in xylene is prepared by following the procedure of Example 4, above. About 75% of the xylene is distilled off, and a quantity of ethylene dichloride equivalent to the xylene remaining in the reaction mixture is added. The reaction mixture is cooled to 60°C., and 1.05 moles of dimethyl sulfate are then added and the mixture is heated to 105°C. to 110°C. and maintained at 105°C. to 110°C. for about 4 hours. The mixture is cooled to 50°C. and triethylamine (8 mole percent based on dimethyl sulfate) is added. The reaction mixture is stirred at 50°C. for 30 minutes. The reaction mixture is cooled to room temperature and then filtered and washed with xylene, then with acetone, and the product dried. A 90% yield of product is obtained.

EXAMPLE 8

Example 7 is repeated in every detail except that 16 mole percent instead of 8 mole percent of triethylamine based on dimethyl sulfate is employed. It is noted that a similar yield of product is obtained.

EXAMPLE 9

There are reacted 12.5 parts of benzalacetophenone and 3.1 parts (by volume) of hydrazine hydrate in methanol to form 3,5-diphenyl-2-pyrazoline. To the latter is added then 5% palladium on carbon catalyst (2 parts) and the reaction mixture is heated at reflux for 1 hour and 20 minutes. The product, 3,5-diphenylpyrazole, is obtained in 97.8% yield.

EXAMPLE 10

The procedure of Example 9 is repeated in every detail except that 1.0 part catalyst is used and the solvent is isopropanol. Following refluxing for 4 ½ hours, 3,5-diphenylpyrazole is obtained in 90.7% yield.

EXAMPLE 11

Benzalacetophenone (12.5 parts) is reacted with hydrazine hydrate (3.1 parts by volume) in methanol to form 3,5-diphenyl-2-pyrazoline. Panasol AN-2 (30 ml), nitrobenzene (7.4 parts) and 5% palladium on carbon catalyst (2 parts) are then added and the mixture heated. Following the distillation of methanol and water from the reaction mixture, the temperature is raised to 200°C. and held at that temperature for 24 hours. The mixture is then cooled to 50°C., filtered, and the catalyst bearing cake of 3,5-diphenylpyrazole is 79.5%, m.p. 194°C. to 199°C.

EXAMPLE 12

The procedure of Example 11 is repeated, except that 5% palladium on carbon catalyst (2 parts) is substituted for the platinum on carbon catalyst, and the reaction mixture is held at 200°C. for 20 hours. 3,5-Diphenylpyrazole is obtained in 70.4% yield.

EXAMPLE 13

The procedure of Example 12 is repeated, except that no nitrobenzene is added to the reaction mixture and the amount of 5% palladium on carbon catalyst is reduced to 0.1 part. Following a 6 ¼ hours hold at 200°C., 3,5-diphenylpyrazole is obtained in 78.7% yield.

EXAMPLE 14

The procedure of Example 13 is repeated, except that Humble Aromatic 150 solvent is substituted for Panasol AN-2 in the dehydrogenation step. Following a 4 hours hold at 200°C., 3,5-diphenylpyrazole is obtained in 41.5% yield.

EXAMPLE 15

The procedure of Example 14 is repeated, except that the dehydrogenation step is carried out under a nitrogen atmosphere and the hydrogen formed in the reaction is purged with nitrogen. Following a 1 ½ hours hold at 200°C., 3,5-diphenylpyrazole is obtained in 89.3% yield.

EXAMPLE 16

The procedure of Example 15 is repeated except the solvent used in the dehydrogenation step is toluene. After 4 ½ hours at reflux, 3,5-diphenylpyrazole is obtained in 91.0% yield.

EXAMPLE 17

3,5-Diphenyl-2-pyrazoline (21.9 parts) is dissolved in ethylene dichloride (75 parts by volume). There is next added 5% palladium on carbon catalyst (4 parts containing 40% water) is added and the mixture is heated at reflux for 8 hours. There is obtained 3,5-diphenylpyrazole in a 79.3% yield whose melting point ranges from 196°C. to 200°C.

EXAMPLE 18

To a suitable reaction vessel are added 42 parts of benzalacetophenone which is slurried in 130 parts (by volume) of methanol and 20 parts of water at room temperature. The latter mixture is next purged with nitrogen and 13 parts of 85% hydrazine hydrate are added rapidly to form 3,5-diphenyl-2-pyrazoline. The mixture is heated to reflux and 105 parts of the methanol-water mixture is distilled, 130 parts of xylene are next added, the aqueous phase is removed, and the organic phase is washed with water. There is then added 0.2 part of 5% Pd/alumina under $N_2$, a nitrogen blanket. The mixture is heated to reflux. Following a 2 hour reflux, the mixture was cooled to 10°C. The catalystcontaining solid 3,5-diphenylpyrazole is isolated by filtration, washed with hexane and air-dried. 3,5-Diphenylpyrazole melting at 198° – 201.5°C. was obtained in a 90.1% yield.

EXAMPLE 19

The procedure of Example 18 is followed except that 2 parts of 5% palladium on barium sulfate are used in lieu of the palladium on alumina Example 18. Following a 2 ½ hour of reflux, unreacted 3,5-diphenyl-2-pyrazoline is found to amount to 2.4%, and a 76.4% yield of 3,5-diphenylpyrazole, melting at 198° – 201°C. is obtained.

EXAMPLE 20

The procedure of Example 19 is followed except that 0.4 part palladium black (100% Pd) is used as the catalyst. Following 4 hours reflux, unreacted 3,5-diphenyl-2-pyrazoline is recovered in a yield of 1.1%, and a 88.9% yield of 3,5-diphenylpyrazole melting at 197°–201°C. is obtained.

We claim:

1. A method for the preparation of 3,5-disubstituted pyrazole having the formula:

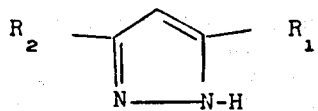

wherein $R_1$ is said Y, Y', Z and Z' each represents a member selected from the group consisting of hydrogen, halogen, methylthio, methysulfonyl, cyano, carboxyl, carboalkoxy $C_1$–$C_4$, hydroxy, alkyl $C_1$–$C_4$, haloalkyl $C_1$–$C_4$ containing 1 to 4 halogen atoms and alkoxy $C_1$–$C_4$ which comprises the steps of: reacting approximately equimolar amounts of a compound having the formula $R_1COCH_3$ with a compound having the formula $R_2CHO$, wherein $R_1$ and $R_2$ are as defined above, in the presence of a $C_1$–$C_4$ alcoholic solvent and a base at a temperature ranging between about 10°C. and 70°C., acidifying said reaction mixture to a pH of at least 7, treating the so-acidified reaction mixture with from about 1.0 to 2.0 mole equivalents of hydrazine, adding to said reaction mixture a dehydrogenation catalyst heating said mixture to refluxing temperatures, and recovering the desired 3,5-disubstituted pyrazole in good yield and purity.

2. The method according to claim 1 wherein the catalyst is selected from the group consisting of platinum, palladium, platinum on alumina, platinum on barium sulfate, palladium on alumina, palladium on barium sulfate, palladium on carbon, palladium on silica, platinum on silica platinum on carbon and pre-reduced copper chromite.

3. The method according to claim 1 wherein said catalytic dehydrogenation reaction is carried out in the presence of an inert gas.

4. A method according to claim 1, which comprises: reacting equimolar amounts of said ketone and said aldehyde in the presence of a $C_1$–$C_4$ alcohol and aqueous sodium hydroxide or potassium hydroxide at a temperature ranging from 20°C. to 30°C., acidifying said reaction mixture with a mineral acid to pH ranging from 5 to 7, said acid being selected from the group consisting of hydrochloric acid, sulfuric acid and phosphoric acid, and treating said mixture with from 1.0 to 2.0 mole equivalents of hydrazine hydrate while maintaining the temperature of said mixture between 20°C. and 30°C., distilling off a portion of the alcohol and adding to the remaining mixture an amount of an aromatic solvent, a cyclic ether, a chlorinated hydrocarbon, or a mixed xylene in an amount equal to about the alcohol removed, water washing the resulting mixture, admixing therewith a dehydrogenation catalyst, refluxing the resulting mixture, azeotropically distilling off water from the reaction mixture, hot filtering said mixture, cooling the filtrate from said filtration, and recovering the 3,5-disubstituted pyrazole from said filtrate.

5. The method according to claim 2, wherein the catalyst employed is platinum on carbon, and the hydrazine reaction and catalytic dehydrogenation are conducted under a blanket of inert gas.

6. The method according to claim 2, wherein the catalyst employed is palladium on carbon.

7. The method according to Claim 2, wherein the catalyst is palladium on silica.

8. The method for the preparation of 3,5-diphenylpyrazole according to claim 1 which comprises: reacting equimolar amounts of acetophenone and benzaldehyde in the presence of a base and a $C_1$–$C_4$ alcohol solvent, at a temperature between about 10°C. and 70°C., acidifying said reaction mixture to a pH of 7 or below with a mineral acid, treating the acidified reaction mixture with from about 1.0 to 1.5 mole equivalents of hydrazine under a blanket of an inert gas selected from the group consisting of nitrogen, argon, helium and carbon dioxide, while maintaining the temperature of the reaction mixture between about 10°C. and 70°C., separating from about 65% to 90% of said $C_1$–$C_4$ alcohol solvent from the reaction mixture and admixing with the remainder of the reaction mixture an amount of solvent approximately equal to the alcohol separated therefrom and selected from the group consisting of an aromatic solvent, a chlorinated hydrocarbon, and an ether, maintaining the said mixture under a blanket of inert gas selected from the group consisting of nitrogen, argon, helium and carbon dioxide, adding a catalyst selected from the group consisting of platinum, palladium, platinum on alumina, platinum on barium sulfate, palladium on alumina, palladium on barium sulfate, palladium on carbon, palladium on silica, platinum on silica, pre-reduced copper chromite and platinum on carbon to the reaction mixture, said mixture being brought to reflux temperatures, removing water azeotropically from said mixture, cooling said mixture to between 100°C. and 130°C., filtering the latter to remove catalyst therefrom, further cooling said filtrate to about 10°C., whereby the 3,5-diphenylpyrazole precipitates, and thereafter recovering said pyrazole from the reaction mixture.

9. The method for the preparation of 3,5-diphenylpyrazole according to claim 1 which comprises: reacting equimolar amounts of acetophenone and benzaldehyde in the presence of methanol and an aqueous base selected from the group consisting of sodium hydroxide and potassium hydroxide at a temperature between 20°C. and 30°C., acidifying said reaction mixture with a mineral acid to pH 5 to 7, said acid being selected from the group consisting of hydrochloric acid sulfuric acid and phosphoric acid, treating said mixture with from 1 to 1.5 mole equivalents of hydrazine hydrate under an inert gas blanket selected from the group consisting of nitrogen, argon, helium and carbon dioxide, maintaining the temperature of said mixture between 20°C. and 30°C., distilling from 75% to 80% of the methanol and adding to the remaining mixture an amount of mixed xylenes equal to about the methanol removed, water washing the resulting mixture and admixing therewith under said inert gas blanket palladium on carbon catalyst, refluxing the resulting mixture at a temperature between 130°C. and 150°C., azeotropically distilling off water from the reaction mixture, adding dimethylformamide to the resulting mixture, filtering said mixture to separate said catalyst therefrom, and recovering a filtrate containing 3,5-diphenylpyrazole.

10. The method according to claim 9, wherein methanol is used as the solvent in the reaction of acetophenone and benzaldehyde and mixed ortho and paraxylenes are employed to effect the catalytic dehydrogenation.

11. In a method for the preparation of a 3,5-disubstituted pyrazole having the formula of Claim 1:

wherein $R_1$ is

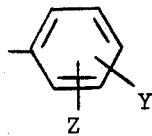

and $R_2$ is

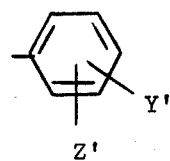

and Y, Y', Z and Z' each represents a member selected from the group consisting of hydrogen, halogen, methylthio, methylsulfonyl, cyano, carboxyl, carboalkoxy $C_1$–$C_4$, hydroxy, alkyl $C_1$–$C_4$, haloalkyl $C_1$–$C_4$ containing 1 to 4 halogen atoms and alkoxy $C_1$–$C_4$; the improvement which comprises the steps of: heating a pyrazoline compound having the structure:

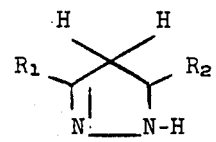

wherein $R_1$ and $R_2$ are each as defined above, in the presence of a solvent and a dehydrogenation catalyst selected from the group consisting of platinum, palladium, platinum on alumina, platinum on barium sulfate, platinum on carbon, palladium on alumina, palladium on barium sulfate, palladium on carbon, platinum on silica, palladium on silica and prereduced copper chromite.

* * * * *